United States Patent [19]

Borror et al.

[11] 4,195,180

[45] Mar. 25, 1980

[54] SULFAM (NA) PHTHALEINS

[75] Inventors: Alan L. Borror, Lexington; Louis Cincotta, Andover; Ernest W. Ellis, Carlisle; James W. Foley, Andover, all of Mass.

[73] Assignee: Polaroid Corporation, Cambridge, Mass.

[21] Appl. No.: 836,067

[22] Filed: Sep. 23, 1977

[51] Int. Cl.² .................. C07D 275/06; C07D 417/10; C07D 279/02
[52] U.S. Cl. .................................... 544/33; 544/135; 544/368; 546/198; 260/243.3; 96/84 R; 544/58.7; 544/207; 430/510
[58] Field of Search ..................... 260/304 A, 293.57; 544/33, 135, 368

[56] References Cited

U.S. PATENT DOCUMENTS 3,702,244  11/1972  Bloom et al. ............................... 96/3

OTHER PUBLICATIONS

Beilstein, "Hand buch der Organischen Chemie", vol. 27, p. 534.
Dutt, S., J. Chem. Soc., 121, pp. 2389-2394 (1922).
Abramaitch, R., J. Chem. Soc., Perkin Translation I, 22, pp. 2589-2594 (1974).

*Primary Examiner*—Donald G. Daus
*Assistant Examiner*—Lisa Jones
*Attorney, Agent, or Firm*—Sybil A. Campbell

[57] ABSTRACT

This invention relates to 1-naphthol sulfam(na)phthaleins possessing a carbonyl moiety on the N atom of sulfam(na)phthalein ring, which compounds find utility, for example, as antihalation and filter dyes in photographic products and processes.

9 Claims, No Drawings

SULFAM (NA) PHTHALEINS

BACKGROUND OF THE INVENTION

1. Field of the Invention

This invention relates to novel chemical compounds and, more particularly, it relates to novel sulfam(na)phthaleins useful as antihalation dyes and filter dyes in photographic products and processes.

2. Description of the Prior Art

It is well known to use light-screening dyes in photographic elements. Such a dye may be incorporated as a filter dye in a light-sensitive emulsion layer(s) or in a layer coated over one or more light-sensitive emulsion layers or between two differently color-sensitized emulsion layers to modify the light record in the emulsion layer or to control the spectral composition of light falling on the underlying light-sensitive layer, or it may be incorporated as an antihalation dye in a non-light-sensitive layer positioned on either side of a support carrying the light-sensitive layer(s).

The dyes employed for these purposes, in addition to having the requisite spectral absorption characteristics for their intended use, should be photochemically inert, that is, they should not have any adverse effect on the properties of the light-sensitive emulsion layer(s), and also, they should be capable of being decolorized or removed during photographic processing so as not to leave stain in the processed photographic element. In photographic processes where the dye is removed by being dissolved in a processing solution, it is usually preferred that the dye also decolorize in order to avoid contamination of the processing solution and to prevent staining from residual dye in the processed light-sensitive element.

Though various classes of dyes have been proposed for use in antihalation and color correction filter layers, the dyes heretofore employed have not been altogether satisfactory. Some of the dyes tend to reduce sensitivity, fog or exert other adverse effect on the light-sensitive material. However, the major drawback of previously employed dyes is their tendency to cause stain due to incomplete decolorization or reversal of some of the decolorized form to the original colored form. For example, some classes of dyes rely on the presence of a reagent, such as, a sulfite for "bleaching", i.e., decolorization and unless the dyes are removed from the light-sensitive material during or after processing, their color reappears with a reduction in sulfite concentration.

Dutt, J. Chem. Soc., 121, p. 2389 (1922) reported the condensation of saccharin with aromatic amines and phenols in the presence of concentrated sulfuric acid and also in the presence of fused zinc chloride. The resulting condensation products with saccharin were named "sulfamphthaleins" by analogy to "phthaleins" and "sulfonephthaleins". Though the structure 3,3-di(4'-hydroxyphenyl)-2,3-dihydrobenz[d]isothiazole-1,1-dioxide (named "phenolsulfamphthalein") was assigned to the condensation product obtained with saccharin and phenol, it has been determined that the compound corresponding to the proposed structure has properties different from those reported, for example, colorless rather than pink in alkali. Also, it has been found that the compound correspond to the structure given could not be synthesized by repeating the procedures reported by Dutt.

The present invention is concerned with a novel class of sulfam(na)phthaleins derived from 1-naphthols which class of sulfam(na)phthaleins include compounds useful as light-screening dyes in photography that are free from the drawbacks associated with prior light-screening dyes.

SUMMARY OF THE INVENTION

It is therefore the primary object of the present invention to provide novel sulfam(na)phthaleins.

It is a further object of the present invention to provide novel sulfam(na)phthaleins useful as indicator dyes and/or as antihalation dyes and filter dyes in photographic products and processes.

Other objects of this invention will in part be obvious and will in part appear hereinafter.

The invention accordingly comprises the products and compositions possessing the features, properties and the relation of elements which are exemplified in the following detailed disclosure, and the scope of the application of which will be indicated in the claims.

According to the present invention, novel 3,3-disubstituted sulfam(na)phthaleins are provided which possess certain substituents on the N atom, i.e., in the 2-position of the sulfam(na)phthalein ring. The 3,3 substituents may be the same or different, and at least one of the 3,3 substituents is a 4'-OP-1'-naphthyl moiety and the other is a naphthyl moiety, which may be substituted or unsubstituted. These compounds will be defined with greater particularity hereinafter.

Depending upon the 2-substituent of the sulfam(na)phthalein ring, some of the compounds of the present invention function as classical pH-sensitive indicator dyes, i.e., they have reversibly alterable spectral absorption characteristics in response to changes in pH. Below a given alkaline pH, they have a yellow form, and in the presence of base above said alkaline pH, they are converted to a blue form which is reversed to the original yellow form by reducing the pH below said given alkaline pH.

The remaining compounds, which comprise a preferred embodiment of the present invention, also have a yellow form which is converted to a blue form above a given alkaline pH, but unlike the former compounds, the blue form decolorizes by undergoing an irreversible cleavage reaction with base at a pH above said alkaline pH to yield a colorless product. Because of their ability to decolorize completely and irreversibly in base above a predetermined pH without requiring a reagent, such as, a sulfite for the "bleaching" reaction and because the colorless product produced upon irreversible cleavage is inert to changes in pH, the compounds may be retained in the photographic light-sensitive element without the possibility of color reappearing in time. Besides being non-staining, the compounds are inert with respect to the light-sensitive material and thus, may be positioned in a layer adjacent to a silver halide emulsion layer or directly incorporated into an emulsion layer without having any adverse effect on the properties of the emulsion.

For a fuller understanding of the nature and objects of the present invention, reference should be had to the following detailed description.

DETAILED DESCRIPTION OF THE INVENTION

The novel compounds provided by the present invention may be represented by the formula

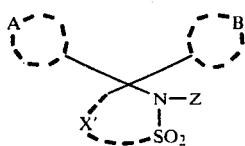

wherein A is a 4'-hydroxynaphthyl moiety; B is a naphthyl moiety; X' represents the atoms necessary to complete a ring-closing moiety selected from a sulfamphthalein moiety and a sulfamnaphthalein moiety; and Z is a moiety possessing a

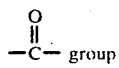

bonded to said N atom. Examples of said Z moieties are those represented by the formula

wherein R is selected from methyl, methyl substituted with at least one halo group selected from chloro, bromo and fluoro, alkoxy having 1 to 4 carbon atoms, phenyl, phenyl substituted preferably in the para position with alkyl having 1 to 4 carbon atoms or —N,N—(-dialkyl)amino, phenyl substituted with at least one electron-withdrawing group, phenoxy, phenoxy substituted with at least one electron-withdrawing group, phenyl substituted in the ortho position with —CH$_2$R$^{10}$ wherein R$^{10}$ is chloro or bromo, and preferably, —O(CH$_2$)$_2$Y wherein Y is an electron-withdrawing group. By "electron-withdrawing group" is meant a group having a positive sigma value as defined by Hammett's Equation.

By "sulfamphthalein" is intended a 2,3-dihydrobenz[-d]isothiazole-1,1-dioxide moiety and by "sulfamnaphthalein" is intended a 2,3-dihydronaphtho[1,8-de]-1,2-thiazine-1,1-dioxide moiety. The respective 2,3-dihydrobenz[d]isothiazole-1,1-dioxide and 2,3-dihydronaphtho[1,8-de]-1,2-thiazine-1,1-dioxide ring-closing moieties are illustrated below:

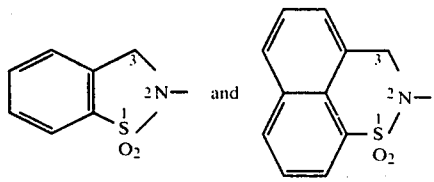

As noted above, the compounds of the present invention are yellow below a predetermined alkaline pH and in the presence of base above said predetermined pH are converted to a blue compound by the removal of the ionizable proton from the functional —OH of the 4'-hydroxynaphthyl moiety which is accompanied by the opening of the sulfam(na)phthalein ring. Where R is said methyl, alkoxy, phenyl, phenoxy, phenyl substituted with alkyl or —N,N(dialkyl)amino or phenyl substituted with at least one electron-withdrawing group, the blue compound is converted back to the original yellow compound by reducing the pH below said predetermined alkaline pH. Where R is methyl substituted with at least one halo group, —(CH$_2$)$_2$Y, phenoxy substituted with at least one electron-withdrawing group or phenyl substituted in the ortho position with —CH$_2$R$^{10}$, the blue compound produced is converted to a new compound, which is colorless, by irreversible cleavage of the N-substituent of the sulfam(-na)phthalein ring after remaining in contact with said base above a predetermined alkaline pH, usually pH 10, for a predetermined time. The new compound produced, which possesses a different substituent on the N atom of the sulfam(na)phthalein ring, is different from the blue compound and from the yellow precursor compound and is non-reversible to either the blue compound or the yellow precursor by changes in pH.

It will be understood that the A moiety and/or the B moiety and/or the ring-closing moiety of the compounds represented in formula I above may contain one or more substituents in addition to those specified, which substituents should not interfere with the intended use of the compounds.

Typical substituents include branched or straight chain alkyl, such as, methyl, ethyl, isopropyl, n-butyl, t-butyl, hexyl, octyl, dodecyl, hexadecyl, octadecyl and eicosanyl; aryl, such as phenyl and naphthyl; alkaryl and aralkyl, preferably, alkyl-substituted phenyl and phenyl-substituted alkyl, such as p-ethylphenyl, p-octylphenyl, p-dodecylphenyl, benzyl, phenethyl, phenylhexyl and phenyldodecyl; alkoxy, such as, methoxy, ethoxy, butoxy, octadecyloxy, 1-ethoxy-2-($\beta$-ethoxyethoxy); aryloxy, such as, phenoxy, benzyloxy and naphthoxy; alkoxyalkyl, such as, methoxymethyl, ethoxymethyl, and dodecyloxyethyl; halo, such as, fluoro, bromo and chloro; trihalomethyl, such as, trifluoromethyl and trichloromethyl; sulfonamido (—N-H—SO$_2$R$^o$ wherein R$^o$ is alkyl, aryl, alkaryl or aralkyl); sulfamoyl (—SO$_2$—NH—R$^o$ wherein R$^o$ has the same meaning given above); acyl

wherein R$^o$ has the meaning given above); sulfonyl (—SO$_2$—R$^o$ wherein R$^o$ has the same meaning given above); sulfo; cyano; carboxy; hydroxy; and amino including mono- and disubstituted amino (—NR'R" wherein R' and R" each are hydrogen, alkyl, aryl, alkaryl or aralkyl and R' and R" taken together represent the atoms necessary to complete a saturated heterocyclic ring, such as piperidino, pyrrolidino, N-lower alkylpiperazino, morpholino, thiomorpholino and tetrahydro-2H,4H-1,3,6-dioxazocino).

In a preferred embodiment, the compounds of the present invention may be represented by the formula

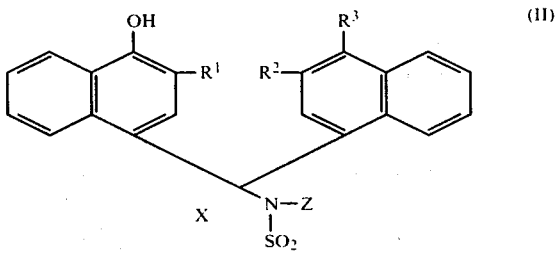

wherein $R^1$ and $R^2$ each are selected from hydrogen, alkyl, alkoxy, chloro and fluoro; $R^3$ is selected from hydrogen, hydroxy, alkyl, alkoxy, —N,N—(dialkyl)amino, —N,N—(w-$R^8$alkyl)$_2$-amino wherein $R^8$ is hydroxy or halo, preferably chloro, —NHCOCH$_3$, piperidino, pyrrolidino, N-methylpiperazino, morpholino, thiomorpholino or tetrahydro-2H,4H-1,3,6-dioxazocino; X represents the atoms necessary to complete 2,3-dihydrobenz[d]isothiazole-1,1-dioxide or 2,3-dihydronaphtho[1,8-de]-1,2-thiazine-1,1-dioxide; and Z has the same meaning given above. Preferably Z is $$-\overset{O}{\underset{\|}{C}}O(CH_2)_2Y$$

wherein Y is an electron-withdrawing group preferably having a positive sigma value greater than 0.60.

Usually, the alkyl and alkoxy substituents comprising $R^1$, $R^2$ and $R^3$ are lower alkyl having 1 to 4 carbon atoms, such as, methyl, ethyl, n-propyl, isopropyl and n-butyl and lower alkoxy having 1 to 4 carbon atoms, such as, methoxy, ethoxy, propoxy and butoxy. Also, the alkyl groups of the —N,N—(dialkyl)amino and —N,N-(w-$R^8$alkyl)$_2$amino substituents comprising $R^3$ usually are lower alkyl having 1 to 4 carbon atoms. Preferred electron-withdrawing groups, Y, include

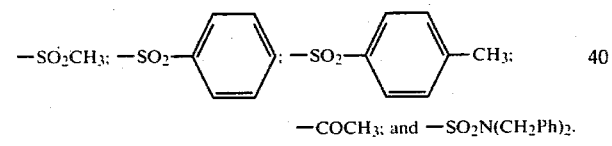

The sigma value for these and other groups have been reported by Eugen Muller, Methoden Der Organischen Chemie, Georg Thieme Verlag, Stuttgart, 1970, p. 78.

In a particularly preferred embodiment, X in formula (II) above represents the atoms necessary to complete 2,3-dihydrobenz[d]isothiazole-1,1-dioxide.

Specific examples of compounds within the scope of the present invention are as follows:

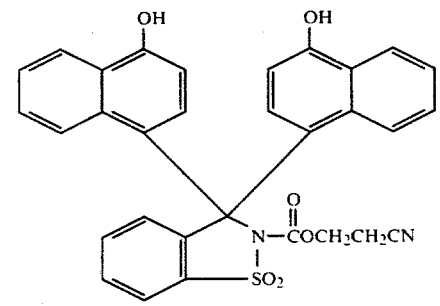

(1)

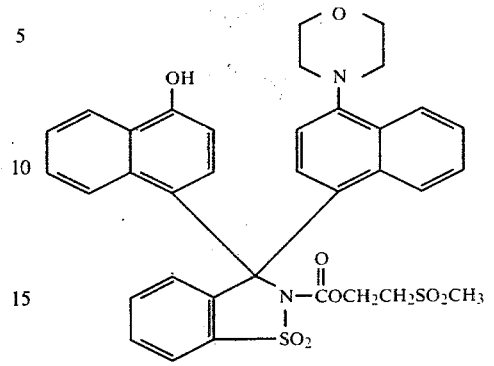

(2)

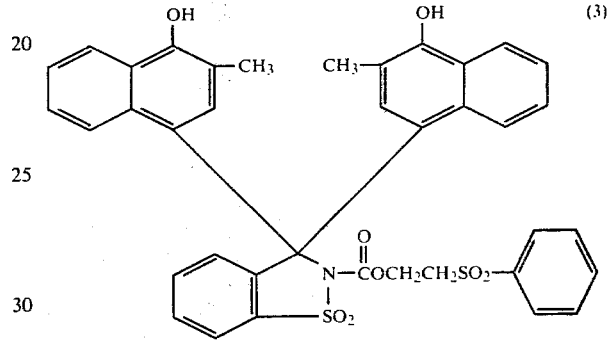

(3)

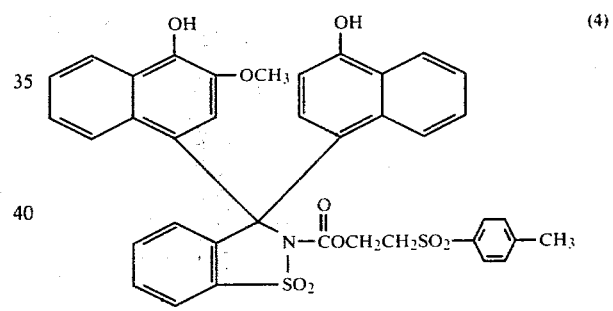

(4)

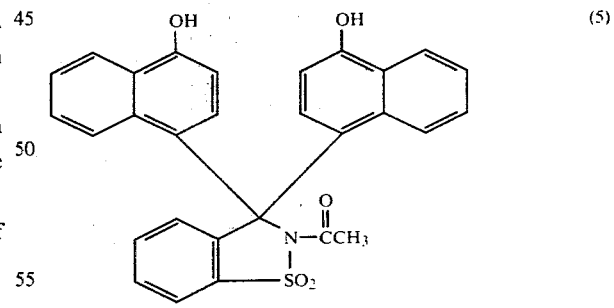

(5)

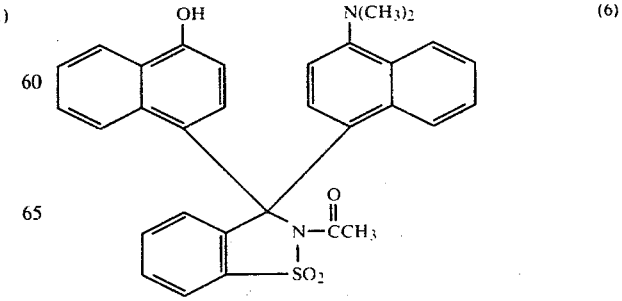

(6)

-continued

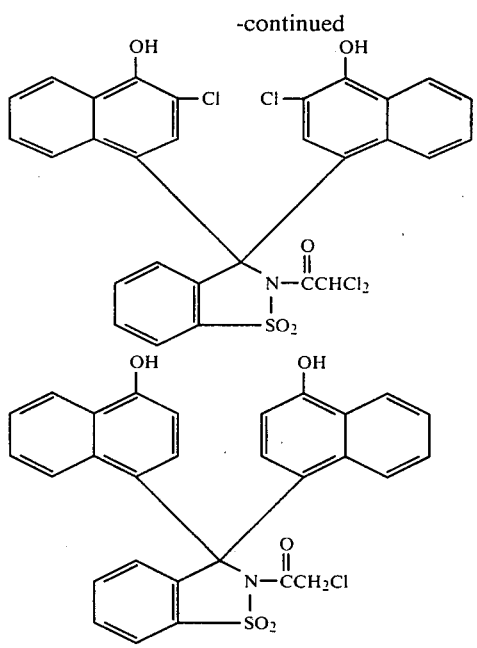

The compounds of the present invention may be prepared by reacting (a) a 3-(4'-OP-1'-naphthyl)-3-(naphthyl)-2,3-dihydrobenz[d]isothiazole-1,1-dioxide wherein P is a protecting group compatible with organometallic reagents and (b) an acylating agent, W-Z wherein W is chloro or bromo and Z is said carbonyl moiety in pyridine to give the corresponding 2-Z-3,3-disubstituted-2,3-dihydrobenz[d]isothiazole-1,1-dioxide. The N-acylated compound is then treated with weak acid to remove the protecting group(s) to yield the 3,3-disubstituted-2,3-dihydrobenz[d]isothiazole-1,1-dioxide product. Optionally, the N-acylation step may be conducted by sequentially reacting (a) with an alkali metal hydride to form the corresponding N-alkali metal salt followed by reaction with the acylating agent. The compounds containing a 2,3-dihydronaphtho[1,8-de]-1,2-thiazine-1,1-dioxide as the ringclosing moiety are prepared by employing a 3-(4'-OP-1'-naphthyl-3-(naphthyl)-2,3-dihydronaphtho[1,8-de]-1,2-thiazine-1,1-dioxide in the foregoing procedure. The above described method of synthesizing the compounds of the present invention forms the subject matter of coupling U.S. patent application Ser. No. 836,010 of Stanley M. Bloom, Alan L. Borror and James W. Foley filed concurrently herewith.

The 3-(4'-OP-1'-naphthyl)-3-(naphthyl)-2,3-dihydrobenz[d]isothiazole-1,1-dioxides employed as the intermediates, (a), in the above method may be synthesized by reacting a 3-(4'-OP-1'-naphthyl)-benz[d]isothiazole-1,1-dioxide and a naphthyllithium reagent as disclosed and claimed in copending U.S. patent application Ser. No. 836,008 of Alan L. Borror, Louis Cincotta, James W. Foley and Marcis M. Kampe filed concurrently herewith. The 3-(4'-OP-1'-naphthyl)benz[d]isothiazole-1,1-dioxide is prepared by converting a blocked 4-halo-1-naphthol to the corresponding Grignard or lithium reagent and then reacting this reagent with saccharin or saccharin pseudo-chloride. 3-(4'-OP-1'-naphthyl)benz[d]isothiazole-1,1-dioxides form the subject matter of copending U.S. patent application Ser. No. 836,024 of Alan L. Borror, Louis Cincotta, Ernest W. Ellis, James W. Foley and Marcis M. Kampe filed concurrently herewith.

The method of aforementioned application Ser. No. 836,008 is useful in synthesizing intermediates for the subject compounds wherein the A and B moieties are either the same or different. Intermediates for the subject compounds wherein the A and B moieties are the same, i.e., identical, also may be prepared by reacting two equivalents of a blocked 1-naphthol as a Grignard reagent with one equivalent of 3-chlorobenz[d]isothiazole-1,1-dioxide (or 3-chloronaphtho-[1,8-de]-1,2-thiazine-1,1-dioxide) as disclosed and claimed in copending U.S. patent application Ser. No. 836,004 of Stanley M. Bloom, Alan L. Borror and James W. Foley filed concurrently herewith.

As discussed in the aforementioned applications, the protecting groups selected for preparing the blocked 1-naphthols and for blocking other substituents as may be necessary should be compatible with lithium and Grignard reagents and should protect the hydroxyl and other groups against reaction under conditions encountered in the synthesis of the starting materials and the intermediates and in the subsequent steps in the synthesis of the products. In addition, the protecting group(s) selected should be capable of being easily removed under neutral or weakly acid conditions to regenerate the hydroxyl and other groups and yield the desired product.

Where the B moiety of the subject compounds is other than a 4'-OH-naphthyl moiety, they also may be synthesized by the method forming the subject matter of copending U.S. patent application Ser. No. 836,025 of Alan L. Borror, James W. Foley, Marcis M. Kampe and John W. Lee, Jr. filed concurrently herewith. As disclosed and claimed therein, the method comprises reacting a 3-(naphthyl)-benz[d]isothiazole-1,1-dioxide and a 4'-OP-naphthyllithium compound to give the corresponding 3-(naphthyl)-3-(4'-OP-1'-naphthyl)-2,3-dihydrobenz[d]isothiazole-1,1-dioxide wherein P represents a protecting group compatible with organometallic reagents. The compound thus prepared is then reacted with the selected carboxylic acid halide to give the corresponding 2-carbonyl derivative which is then treated with acid to remove the protecting group and yield the product. The naphthyl group of the 3-(naphthyl)-benz[d]isothiazole-1,1-dioxide employed in the initial step of the synthesis may be unsubstituted, or it may be substituted with, for example, an N-heterocyclic moiety and/or other substituents. 3-(Naphthyl)-benz[d]isothiazole-1,1-dioxides wherein the naphthyl substituent is substituted with certain N-heterocyclic moieties form the subject matter of copending U.S. patent application Ser. No. 836,022 of Alan L. Borror, James W. Foley and John W. Lee, Jr. filed concurrently herewith.

For convenience, the specifications of aforementioned applications Ser. Nos. 836,004; 836,008; 836,024; 836,022; 836,025; and 836,010 are incorporated herein.

The following example is given to further illustrate the present invention and is not intended to limit the scope thereof.

Preparation of the compound having the formula:

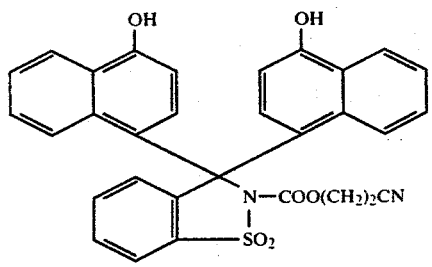

(a) To a solution of 168 mg. of potassium t-butoxide in 5 ml. of dry tetrahydrofuran was added 834 mg. of 3,3-di[4'-(2''-tetrahydropyranyloxy)-1'-naphthyl-2,3-dihydrobenz[d]isothiazole-1,1-dioxide] in several small portions under nitrogen. The yellow-brown solution obtained was stirred for 2 hours at room temperature and then cooled in an ice bath.

(b) To the cooled solution of step (a) was added dropwise 267 mg. of β-cyanoethylchloroformate. (The color changed to light yellow.) The resulting solution was stirred over the weekend at room temperature under nitrogen during which time most of the solvent evaporated leaving yellow-orange solids comprising the title compound and beblocked starting material.

(c) The yellow-orange solids were taken up in 25 ml. of ether and the ether solution concentrated to about 10 ml. The crystals that formed were filtered, washed with ether and the orange and yellow components separated by preparative TLC on (silica gel/n-butanol). The orange component was eluted with methanol. The methanol was then evaporated to give the title compound. $\lambda_{max}^{MeOH}$ 455mμ (W½ 403–510mμ), $\lambda_{max}^{MeOH/NaCO_3/H_2O}$ 660 (W½ 585–700mμ).

The intermediate having the formula

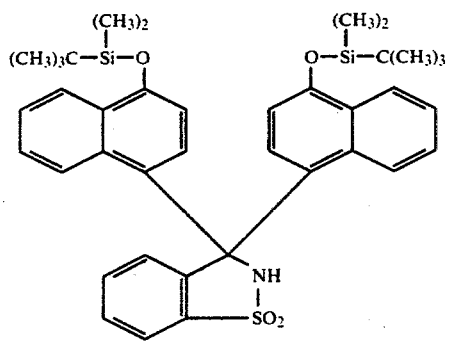

was prepared as follows:

(a) 16.87 g. of 4-bromonaphthyl dimethyl-t-butylsilyl ether was dissolved in 60 ml. of anhydrous ethyl ether under nitrogen, and the solution then cooled to −60° C. in a dry ice-acetone bath. 20.8 ml. of 2.4 N n-butyllithium in hexane was added to the cooled solution dropwise over a period of 15–20 minutes. The reaction mixture was stirred for 30 minutes and allowed to come to 15° C. over 45 minutes.

(b) The solution of step (a) was then cooled back to −40° C., and 4.63 g. of saccharin pseudo-chloride was added portionwise. After addition was complete, the reaction mixture was allowed to warm to room temperature, stirred at room temperature overnight and cooled. 50 ml. of cold water was added followed by the addition of dilute HCl until the pH reached 3–4. The ether phase was separated, and the aqueous phase extracted with 50 ml. of fresh ether. The ether portions were combined, washed with 100 ml. of water, dried over sodium sulfate, filtered and evaporated under reduced pressure. The residue was dissolved in 150 ml. of iso-propanol and the solution slowly poured into 1 liter aqueous HCl solution having a pH of 3. The aqueous phase was decanted leaving a gummy residue. Treatment of the residue with iso-propanol and aqueous HCl (pH 3) was repeated and the final residue was dissolved in 250 ml. of iso-propanol. 3% HCl was added until precipitation ceased. The solution was allowed to stand for 10 min., the solvent decanted and water added to the gummy precipitate which on standing became cyrstalline. The precipitate was filtered and air-dried over the weekend to give 15.55 g. of the title compound.

The dimethyl-t-butylsilyl ether of 4-bromo-1-naphthol was prepared as follows:

4-Bromo-1-naphthol (22.1 g.) and dimethyl-t-butylsilyl chloride (18.1 g.) were dissolved in 50 ml. of dry dimethylformamide at room temperature. The resulting solution was cooled in an ice bath and imidazole (17.0 g.) added under nitrogen. (A slight exotherm was observed.) The reaction mixture was stirred overnight.

The reaction mixture was poured into 1500 ml. of water at about 20° C. with stirring. The pH was adjusted to 4–5 with dilute HCl, and the solids were filtered, washed with water, and air dried for 2 hours and then dissolved in 150 ml. of boiling isopropanol. The isopropanol solution was filtered while hot and then cooled slowly to room temperature. Crystals began to form and after standing at room temperature overnight, the solution was cooled in an ice water bath for 1 hour and filtered. The solid collected was washed with small amounts of isopropanol, air dried briefly and then dried in vacuo for 2 hours to give 24.3 g. of the title compound (melting range 70°–73° C.).

The 3,3-di[4'-(2''-tetrahydropyranyloxy)-1'-phenyl]-2,3-dihydrobenz[d]isothiazole-1,1-dioxide having the formula

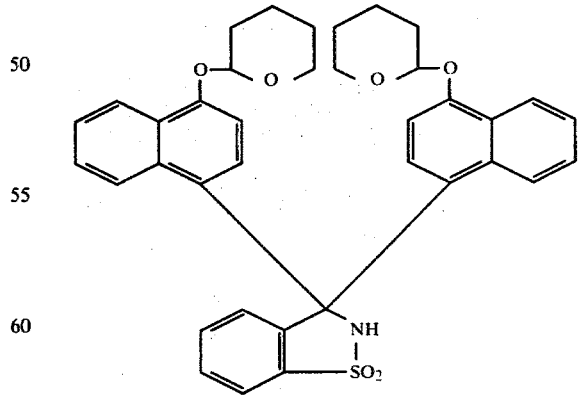

was prepared in the same manner as the foregoing intermediate.

3-[4'-(2''-tetrahydropyranyloxy)-1'-naphthyl]-benz[d]isothiazole-1,1-dioxide having the formula

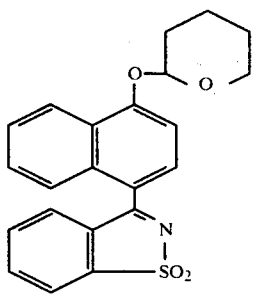

was prepared as follows:

(a) The 2'-tetrahydropyranyl ether of 4-bromo-1-naphthol (1.0 g.) was dissolved in 20 ml. of anhydrous tetrahydrofuran under nitrogen and cooled to −65° C. To this was added 1.37 ml. of n-butyllithium (2.4 M in hexane). The solution, which turned yellow, was stirred for one hour at −65° C.

(b) Saccharin psuedo-chloride (0.65 g.) was added to 30 ml. of tetrahydrofuran at −65° C. and stirred under nitrogen. To the resulting solution was slowly added the solution prepared in step (a). After addition was complete, the reaction mixture was stirred for one hour at −65° C., poured into water, the pH adjusted to 6 with conc. HCl and extracted with ether. The ether was dried and evaporated. TLC of the residue on silica gel with ether showed some 2:1 by-product. Crystallization from ethanol gave 0.2 g. of the title compound as light yellow crystals.

Tetrahydropyranylation of 4-bromo-1-naphthol was carried out as follows:

4-Bromo-1-naphthol (12.16 g.) was mixed with 250 ml. of dichloromethane at room temperature. To the resulting slurry was added 125 ml. of dihydropyran and then 13 drops of conc. HCl were added. The clear, straw-colored reaction solution was stirred at room temperature for approximately 3 hours, transferred to a separatory funnel, washed with about 400 ml. of aqueous 10% sodium hydroxide and the dichloromethane layer dried over anhydrous sodium sulfate. After drying, the dichloromethane solution was filtered through fresh anhydrous sodium sulfate, and the pale straw filtrate was evaporated under reduced pressure leaving 25.9 g. of straw yellow oil. The oil was applied directly to a wet packed SiO$_2$ column (100–200 mesh: 4/1 petroleum ether/ether) and eluted with 4/1 petroleum ether/ether. Twenty-four fractions of about 50 ml. each were collected, and fractions 9–24 were combined and evaporated to give 16.91 g. of straw syrup which upon standing crystallized to give the title compound as pale lemon crystals.

The 2'-tetrahydropyranyl ether of 4-bromo-2-chloro-1-naphthol also was prepared according to the foregoing procedure.

The methoxymethylation of 4-bromo-1-naphthol was carried out as follows:

To a stirred solution of 1.0 g. of 4-bromo-1-naphthol in 20 ml. of chloroform (previously dried over P$_2$O$_5$) were added 20 ml. of dimethoxymethane and 10.0 g. of phosphorus pentoxide. After one hour, the chloroform solution was decanted and stirred with a sodium carbonate solution. The chloroform layer was separated, dried over anhydrous sodium sulfate and evaporated leaving a dark oil which was distilled to give the title compound (boiling range 85°–100° C.-bath temperature/0.1 mm Hg).

It will be appreciated that 3-(4'-OP-1'-naphthyl)-benz[d]isothiazole-1,1-dioxides may be reacted with the selected naphthyl-lithium reagent to give the corresponding 3-(4'-OP-1'-naphthyl)-3-(naphthyl)-2,3-dihydrobenz[d]isothiazole-1,1-dioxide, i.e., sulfamphthaleins where the A and B moieties are different.

Where it is desired to prepare sulfamnaphthaleins, 2,3-dihydro-3-oxo-naphtho[1,8-de]-1,2-thiazine-1,1-dioxide or its pseudo-chloride may be substituted for the saccharin reagent to give the corresponding sulfamnaphthalein intermediates and products. The pseudo-chloride may be prepared from the 3-oxo thiazine by reaction with PCl$_5$ in the same manner as the preparation of saccharin pseudo-chloride.

As mentioned above, the preferred compounds of the present invention are useful as light-screening dyes where dyes that are readily and irreversibly discharged, i.e., decolorized, are necessary or desired. Typically, the preferred compounds may be employed as antihalation dyes in a non-light-sensitive layer of a photographic film unit, usually positioned intermediate a photosensitive silver halide emulsion layer and the film base, i.e., support. Also, they may be employed as filter dyes in multilayered multicolor photographic materials, for example, as yellow filter dyes arranged underneath a blue-sensitive emulsion layer in order that the underlying green-sensitive and red-sensitive emulsion layers may be protected from blue light.

Illustrative film units in which the preferred compounds of the present invention may be advantageously used as antihalation dyes are described, for example, in copending U.S. patent application Ser. No. 383,261, of Edwin H. Land filed July 27, 1973. These film units comprise, in the order in which incident light passes therethrough, an additive multicolor screen, a photosensitive silver halide emulsion layer, an antihalation layer in which the selected compound may be disposed, and preferably, an image-receiving layer. As described therein, exposure of the silver halide layer is accomplished through the screen which possesses optical filter elements selectively transmitting predetermined portions of incident radiation, e.g., red, green and blue light, to the underlying photosensitive silver halide layer. Upon photographic processing with an aqueous alkaline processing composition, soluble silver complex is transferred by diffusion and deposited in a superposed image-receiving layer as a function of the degree of exposure of silver halide behind each filter element. The silver image thus formed may then serve to modulate the quantity of light passing through the filter elements in the reverse direction during projection through a transparent support.

In a preferred embodiment, the image-receiving layer is intermediate the silver halide layer and the multicolor screen and remains in position as part of an integral film unit prior to, during and after formation of the image. The antihalation layer is disposed adjacent to the photosensitive layer on the side opposite the screen and serves to prevent the reflection or back-scattering of incident light which has passed through the photosensitive layer thereby eliminating the exposure of silver halide grains in the photosensitive layer other than those within the intended photoexposure path.

As noted above, the preferred compounds of the present invention also are useful as yellow filter dyes in multilayered, multicolor photographic elements employing a blue-, a green-, and a red-sensitive silver halide layer. These compounds also may be advantageously employed as color correction filter dyes in integral negative-positive diffusion transfer film units wherein the image-receiving layer carrying the color transfer image is not separated from the developed photosensitive layers after processing but both components are retained together as a permanent laminate. Included as part of the laminate is a layer of light-reflecting material, preferably titanium dioxide, positioned between the image-carrying layer and the developed photosensitive layer(s). The light-reflecting layer separating the image-carrying and photosensitive components provides a white background for the transfer image and masks the developed photosensitive layer(s). In addition to these layers, the laminate usually includes dimensionally stable outer layers or supports, at least one of which is transparent so that the resulting transfer image may be viewed by reflection against the background provided by the light-reflecting layer.

In integral negative-positive film units where exposure of the photosensitive component and viewing of the final color transfer image takes place through the same transparent support, such as, the film units described in U.S. Pat. No. 3,415,644 issued Dec. 10, 1968 to Edwin H. Land, the preferred compounds may be disposed, for example, in a layer of the positive, i.e., the image-receiving component or disposed in a layer coated over the image-receiving component for controlling the spectral composition of light which falls upon the underlying silver halide emulsion layers, as described in the copending application of Edwin H. Land, Ser. No. 537,124 filed Dec. 30, 1974.

Whether used as antihalation or color correction filter dyes, the preferred compounds of the present invention when disposed in a processing composition-permeable layer are completely and irreversibly decolorized after remaining in contact with an aqueous alkaline processing composition above a predetermined pH for a predetermined time. For example, the compound prepared in Example 1 above has a half-life (T½) in approximately 1 N NaOH of about 30 seconds. Upon contact with said alkali, it changes from yellow to blue substantially instantaneously and then to colorless. By T½ is meant the time measured for one-half of the blue species to decolorize.

The preferred compounds of the present invention may be incorporated into the appropriate layer of the photographic film unit using any of the techniques known in the art. For instance, the selected compound can be dissolved in the appropriate solvent and then dispersed, in the presence of a wetting agent if desired, in a coating solution containing a hydrophilic colloid binder, e.g., gelatin, and the resulting coating solution applied as the desired layer, for example, coated on a transparent support to provide an antihalation layer. The concentration of compound in the layer may vary depending upon the product in which the filter layer is to be used and may be readily adjusted to provide the optical density necessary for the specific use. It will be appreciated that the preferred compounds of the present invention may be used in combination with each other and also may be used in combination with other light-screening dyes previously employed in antihalation and filter layers.

The remaining compounds of the present invention have reversibly alterable spectral absorption characteristics in response to changes in pH and are useful, e.g., as classical pH indicator dyes to measure changes in pH value. Below a predetermined alkaline pH they have a yellow form which, above said predetermined pH, is converted to a blue form. The blue compound does not undergo irreversible cleavage above said predetermined pH to give a colorless product as with the preferred compounds, but is reversible to the initial yellow compound.

Since certain changes may be made in the above products without departing from the scope of the invention herein involved, it is intended that all matter contained in the above description shall be interpreted as illustrative and not in a limiting sense.

What is claimed is:
1. A compound of the formula

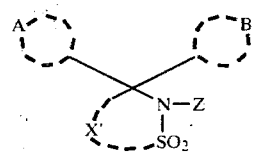

wherein A is a 4'-hydroxynaphthyl moiety; B is a naphthyl moiety; X' represents the atoms necessary to complete a ring-closing moiety selected from a 2,3-dihydrobenz[d]isothiazole-1,1-dioxide moiety and a 2,3-dihydronaphtho[1,8-de]-1,2-thiazine-1,1-dioxide moiety; and Z is the moiety

wherein Y is an electron-withdrawing group selected from —CN, —SO$_2$CH$_3$,

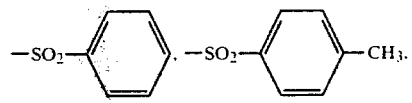

—COCH$_3$ and —SO$_2$N(CH$_2$Ph)$_2$.

2. A compound as defined in claim 1 wherein B is a naphthyl moiety substituted in the 4'-position with —OH.

3. A compound as defined in claim 1 wherein A and B are the same.

4. A compound as defined in claim 1 having the formula

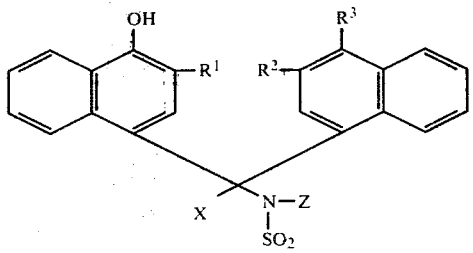

wherein R$^1$ and R$^2$ each are selected from hydrogen, alkyl having 1 to 4 carbon atoms, alkoxy having 1 to 4 carbon atoms, chloro and fluoro; R$^3$ is selected from hydrogen, hydroxy, alkyl having 1 to 4 carbon atoms, alkoxy having 1 to 4 carbon atoms, —N,N—(dialkyl)amino wherein each alkyl contains 1 to 4 carbon atoms, —N,N—(w-R$^8$alkyl)$_2$amino wherein R$^8$ is hydroxy or halo and said alkyl contains 1 to 4 carbon atoms, —NHCOCH$_3$, piperidino, pyrrolidino, N-methylpiperazino, morpholino, thiomorpholino, or tetrahydro-2H,4H-1,3,6-dioxazocino; X represents the atoms necessary to complete 2,3-dihydrobenz[d]isothiazole-1,1-dioxide or 2,3-dihydronaphtho[1,8-de]-1,2-thiazine-1,1-dioxide; and Z has the same meaning given above.

5. A compound as defined in claim 4 wherein R$^1$ and R$^2$ are hydrogen.

6. A compound as defined in claim 5 wherein R$^3$ is hydroxy.

7. A compound as defined in claim 4 wherein R$^3$ is hydroxy.

8. A compound as defined in claim 7 wherein R$^1$ and R$^2$ are chloro.

9. The compound

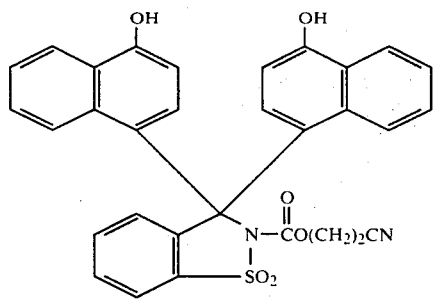

* * * * *